United States Patent
Adachi

(10) Patent No.: US 11,337,847 B2
(45) Date of Patent: May 24, 2022

(54) FECES TREATMENT AGENT FOR COLOSTOMY

(71) Applicant: Excelsior Inc., Tokyo (JP)

(72) Inventor: Kanichi Adachi, Tokyo (JP)

(73) Assignee: EXCELSIOR INC., Tokyo (JP)

( * ) Notice: Subject to any disclaimer, the term of this patent is extended or adjusted under 35 U.S.C. 154(b) by 0 days.

(21) Appl. No.: 16/475,962

(22) PCT Filed: Nov. 2, 2017

(86) PCT No.: PCT/JP2017/039758
§ 371 (c)(1),
(2) Date: Jul. 3, 2019

(87) PCT Pub. No.: WO2018/135089
PCT Pub. Date: Jul. 26, 2018

(65) Prior Publication Data
US 2019/0328571 A1    Oct. 31, 2019

(30) Foreign Application Priority Data
Jan. 17, 2017 (JP) .............................. JP2017-006065

(51) Int. Cl.
*A61F 5/441*  (2006.01)
*A61L 2/23*  (2006.01)

(52) U.S. Cl.
CPC ................ *A61F 5/441* (2013.01); *A61L 2/23* (2013.01)

(58) Field of Classification Search
CPC ............ A61F 5/441; A61F 5/445; A61L 2/23
See application file for complete search history.

(56) References Cited

U.S. PATENT DOCUMENTS

| 6,395,955 B1 * | 5/2002 | Roe .................. A61F 13/42 604/361 |
| 2004/0062681 A1 | 4/2004 | Winston |

(Continued)

FOREIGN PATENT DOCUMENTS

| JP | H10-279978 A | 10/1998 |
| JP | 2004081299 A | 3/2004 |
| JP | 2007000508 A | 1/2007 |

(Continued)

OTHER PUBLICATIONS

EPO, Extended European Search Report for the corresponding European patent application No. 17892352.0, dated Nov. 21, 2019 (8 pages).

(Continued)

*Primary Examiner* — Hong Yu
(74) *Attorney, Agent, or Firm* — Lucas & Mercanti, LLP

(57) ABSTRACT

An object of the present invention is to provide a feces treatment agent for colostomy, which on the assumption that characteristics required as a lubricant are shown, can maintain or improve the feces discharge properties from a colostomy pouch, inhibit the development of feces odor, and improve operativity and portability. A feces treatment agent for colostomy, in which an agent A including (1) a granular water-soluble lubricant, (2) a granular water-absorbing gelling agent, (3) sodium bicarbonate, and (4) a component including at least one selected from the group consisting of zinc oxide, limonite and zinc sulfide is contained in a water-soluble base material.

14 Claims, 2 Drawing Sheets

(56) References Cited

U.S. PATENT DOCUMENTS

2004/0267216 A1    12/2004    Udayakumar et al.
2008/0287896 A1    11/2008    Vega et al.

FOREIGN PATENT DOCUMENTS

| JP | 2007525251 A | 9/2007 |
| JP | 3143047 U | 7/2008 |
| JP | 2010526629 A | 8/2010 |
| JP | 2011503157 A | 1/2011 |
| JP | 2013071107 A1 | 4/2013 |
| JP | 2013165849 A | 8/2013 |
| JP | 2014144399 A | 8/2014 |
| WO | 2013030581 A1 | 3/2013 |

OTHER PUBLICATIONS

PCT, International Preliminary Report on Patentability for the corresponding application No. PCT/JP2017/039758, dated Aug. 1, 2019, with English translation (20 pages).
Hollister product catalogue; 1 page; https://www.hollister.com/japan/products/product_series; Abridged English translation.
International Search Report dated Jan. 23, 2018 for PCT/JP2017/039758 and English translation.
CNIPA, Office Action for the corresponding Chinese patent application No. 201780082096.2, dated Mar. 23, 2021, with English translation.
CNIPA, Office Action for the corresponding Chinese patent application No. 201780082096.2, dated Nov. 16, 2021, with English translation.

\* cited by examiner

[FIG. 1]
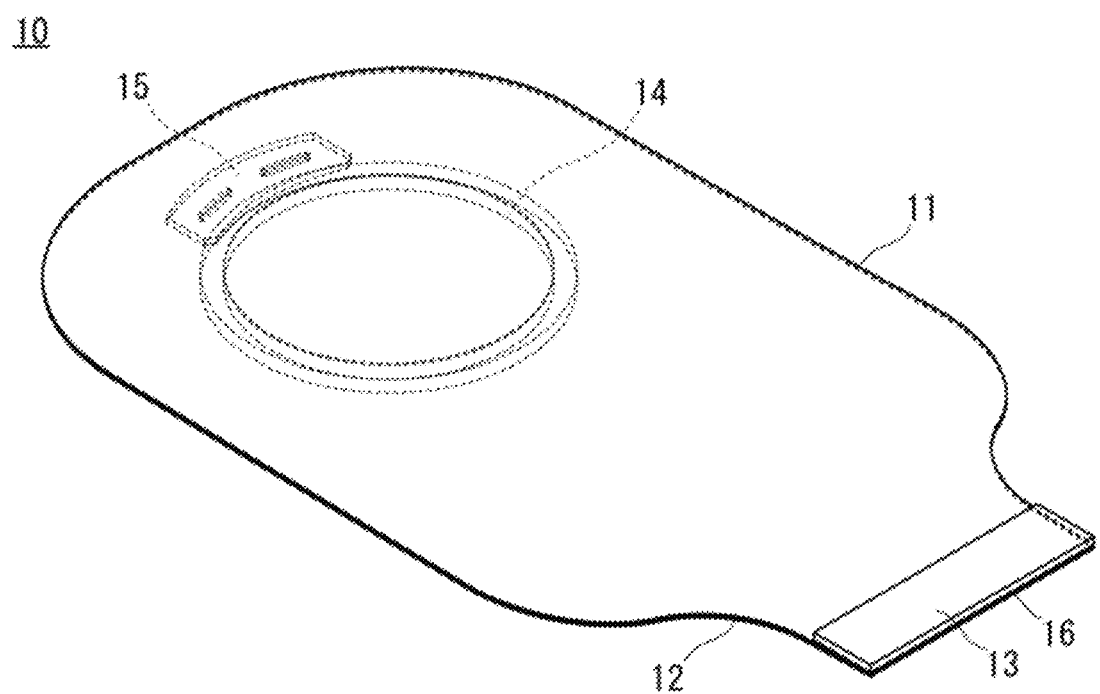

[FIG. 2]
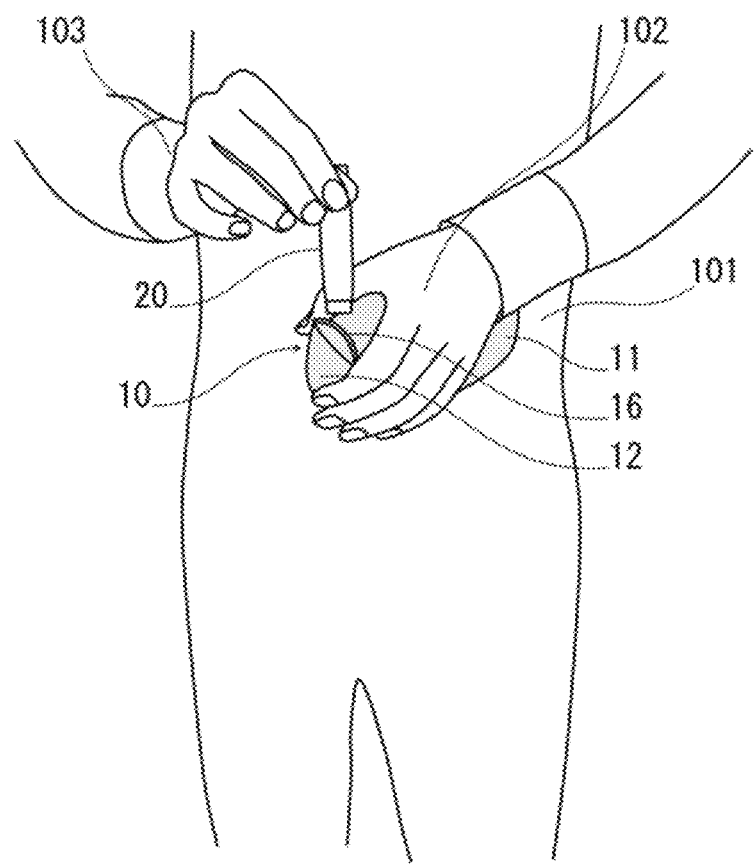

FECES TREATMENT AGENT FOR COLOSTOMY

CROSS REFERENCE TO RELATED APPLICATION

This Application is a 371 of PCT/JP2017/039758 filed on Nov. 2, 2017 which, in turn, claimed the priority of Japanese Patent Application No. 2017-006065 filed on Jan. 17, 2017, both applications are incorporated herein by reference.

TECHNICAL FIELD

The present invention relates to a feces treatment agent for colostomy.

BACKGROUND ART

The final purpose of contemporary medicine is an improvement in post-therapeutic quality of life (QOL). Although patients who underwent stoma construction such as colostomy, ileostomy and urostomy have got away from a life-threatening risk, stoma patients require to routinely attach an ostomy pouch to receive stool and urine.

The ostomy pouch is useful for the patients to lead a normal life; however, on the other hand, many users feel anxious that the odor from feces gives surrounding people an uncomfortable feeling, which is a psychological burden. Because the anxious feeling is also part of the reason that users avoid e.g. going out and a relationship with others, a technique for effectively reducing the odor has been strongly demanded.

On the other side, as a problem in using an ostomy pouch, stool does not smoothly fall to the bottom of the pouch and remain in the upper part because the form of stool is formed inside the body to some extent, and, in some cases, stool is fixed around the stoma portion particularly in colostomy uses (in ileostomy uses, this problem does not often occur because stool is generally watery). That is, there has been a problem in that, because the inner surfaces of a pouch stick to each other, an inflow and downward movement of stool released to the pouch are hindered and feces remain mainly around the stoma portion. In addition, the same problem can develop also in a case where a downward movement of stool is hindered by stool adhering to the inner surface of a pouch. The state as described above not only obstructs excretion and causes health problems, but also deteriorates handleability at the time of removing and attaching a pouch, leading to exposing users and surrounding people to the odor of excreta for a prolonged time, which has been a big problem.

For the problem as described above, an anti-sticking agent and a lubricant for an ostomy pouch are supposed (e.g. Patent Literatures 1 to 3).

In addition, there is also a technique for providing a lubricant composition for an ostomy pouch, which makes an inflow and downward movement of feces smooth, prevents feces from sticking to the inside of the pouch (adhering to the whole inner surface of the pouch), and has excellent deodorant function and usability (Patent Literature 4).

Moreover, a bottle-type deodorant lubricant including purified water, a botanical deodorant component (persimmon tannin extract), a lubricating component, phenoxyethanol and methylparaben to show a deodorant effect and make discharge smooth is also commercially available (Non-patent Literature 1). In addition, a single-use lubricant packet is also suggested (Non-patent Literature 2).

CITATION LIST

Patent Literatures

Patent Literature 1: JP 2004-081299 A
Patent Literature 2: JP 2007-000508 A
Patent Literature 3: JP 2007-525251 W (corresponding to WO 2005/004944)
Patent Literature 4: JP 2013-165849 A Non-patent Literatures
Non-patent Literature 1: Product Information [online] of Coloplast Corp, [searched on Dec. 12, 2016], internet <URL: https://www.coloplast.co.jp/deol-bottle-ja-jp.aspx>
Non-patent Literature 2: Product Information [online] of Hollister Co., Ltd., [searched on Dec. 12, 2016], internet <URL: https://www.hollister.com/japan/products/product_series. asp?id=1&family=9&series=600>

SUMMARY OF INVENTION

Technical Problem

However, there exists a problem in that the odor of feces cannot be completely removed by e.g. lubricants which have been conventionally supposed. Furthermore, the present inventors have recognized that there exist problems in use (portability, operativity) which have not been conventionally recognized.

Therefore, an object of the present invention is to provide a feces treatment agent for colostomy, which can maintain or improve feces discharge properties, inhibit the development of feces odor, and moreover improve operativity and portability.

Solution to Problem

The present inventors diligently investigated to solve the above problems. As a result, the present inventors found that at least one of the problems described above could be solved by providing a feces treatment agent for colostomy, in which an agent A including (1) a granular water-soluble lubricant, (2) a granular water-absorbing gelling agent, (3) sodium bicarbonate, and (4) a component including at least one selected from the group consisting of zinc oxide, limonite and zinc sulfide is contained in a water-soluble base material, thereby completing the present invention.

Advantageous Effects of Invention

According to one embodiment of the present invention, it is possible to provide a feces treatment agent for colostomy, which can maintain or improve feces discharge properties, inhibit the development of feces odor, and moreover improve operativity and portability. In addition, according to one embodiment of the present invention, characteristics required as a lubricant (a proper viscosity, etc.) can be shown.

BRIEF DESCRIPTION OF DRAWINGS

FIG. 1 is a schematic perspective view which shows an example of a colostomy pouch.

FIG. 2 is a schematic view, in which a stoma patient attaching a colostomy pouch opens the outlet with one hand and adds a feces treatment agent for colostomy from the outlet with another hand.

DESCRIPTION OF EMBODIMENTS

The present invention will now be described. It should be noted that the present invention is not limited only to the following embodiments. In addition, in the present description, "X to Y" indicating a range means "X or more and Y or less." In addition, unless otherwise specified, operations and the measurement of e.g. physical properties are measured under the condition of room temperature (20 to 25° C.)/a relative humidity of 40 to 50% RH.

(Feces Treatment Agent for Colostomy)

One embodiment of the present invention is a feces treatment agent for colostomy, in which an agent A including (1) a granular water-soluble lubricant, (2) a granular water-absorbing gelling agent, (3) sodium bicarbonate, and (4) a component including at least one selected from the group consisting of zinc oxide, limonite, lignin, zinc sulfide, slaked lime and limestone is contained in a water-soluble base material. The feces treatment agent for colostomy of this embodiment can maintain or improve feces discharge properties, inhibit the development of feces odor, and moreover improve operativity and portability. In addition, the feces treatment agent for colostomy of this embodiment can show characteristics required as a lubricant (a proper viscosity, etc.) It should be noted that the feces treatment agent for colostomy can be simply referred to as a treatment agent in the present description, in some cases. In addition, a mixture including the component (1), the component (2), the component (3), and the component (4) is provided as "agent A" for the purpose of convenience in the present description, and the "agent A" is a convenient term which can be replaced with, for example, "treatment material", "treatment composition", etc.

As described above, various lubricants which are used by application and spraying have been conventionally supposed to make a downward movement of feces smooth and prevent feces from sticking to the inside of a pouch.

However, when carrying e.g. a bottle containing a lubricant as disclosed in Non-patent Literature 1, portability is bad. It is worse for stoma patients who already have to carry various things related to an ostomy pouch.

Therefore, the present inventors removed a stereotype "carrying [a lubricant]." That is, the treatment agent of one embodiment of the present invention is a treatment agent which can create a deodorant gelling agent (deodorant lubricant) when needed by adding water which can be easily obtained in e.g. a toilet or convenience store by stoma patients themselves. In other words, according to the treatment agent of one embodiment of the present invention, it is not required to carry a lubricant including a liquid or gel accounting for most of its weight on a constant basis, and portability is dramatically improved.

On the other hand, a single-use lubricant packet is also commercially available to improve portability (e.g. Non-patent Literature 2). However, because both hands are required to squeeze a lubricant from the packet, it is inconvenient to open the outlet of a colostomy pouch with both hands full, and operativity is bad.

On the contrary, in the treatment agent of one embodiment of the present invention, a component which subsequently gels by adding water is contained in a water-soluble base material, and thus while the outlet of a colostomy pouch is opened with one hand, the treatment agent according to the present application including the water-soluble base material (with an agent A contained in the water-soluble base material) can be smoothly easily added with another hand, and operativity is dramatically improved (after adding the treatment agent, it is only required to add water prepared on site).

Needless to say, the treatment agent of one embodiment of the present invention contains a deodorant component which is not contained in conventional lubricants, and thus can eliminate the odor which cannot be completely removed by conventional lubricants.

The treatment agent of one embodiment of the present invention includes (1) a granular water-soluble lubricant, and (2) a granular water-absorbing gelling agent. As described above, because the (1) granular water-soluble lubricant and the (2) granular water-absorbing gelling agent are included, an expected technical effect can be shown. In addition, it is thought that proper gelation intended in the present invention proceeds by adding (3) sodium bicarbonate.

In addition, the treatment agent of one embodiment of the present invention includes (4) a component including at least one selected from the group consisting of zinc oxide, limonite and zinc sulfide. It is thought that proper gelation intended in the present invention proceeds by including this component. As described above, it is thought that the component (1) to the component (4) act alone or act in cooperation and accordingly the treatment agent of one embodiment of the present invention can show the expected technical effect of the present invention. However, these mechanisms are matters of speculation, and it is not necessary to say that the technical scope of the present invention is not restricted by the mechanisms.

Embodiments of the treatment agent of the present invention will now be described.

(1) Granular Water-Soluble Lubricant

The treatment agent of the present invention includes an agent A, and the agent A includes a granular water-soluble lubricant as the component (1). In one embodiment of the present invention, it is thought that the gelation ability and viscous properties can be good when the granular water-soluble lubricant acts in cooperation with a granular water-absorbing gelling agent. It should be noted that the total amount of components forming an agent A is 100 mass % in the present description.

The granular water-soluble lubricant which can be included in the treatment agent of one embodiment of the present invention is a granular agent which becomes a lubricant after contact with water. This granular water-soluble lubricant is not particularly restricted, and is water-soluble carboxymethyl cellulose, water-soluble carboxyethyl cellulose, a carboxyvinyl polymer (what is called carbomer), or bentonite.

The average particle diameter of a granular water-absorbing gelling agent in the treatment agent of one embodiment of the present invention is preferably 0.1 to 150 μm, more preferably 1 to 106 μm, further preferably 10 to 80 μm, and still further preferably 20 to 60 μm. In this range, the expected technical effect can be efficiently shown. In addition, as the average particle diameter of a granular water-absorbing gelling agent in the treatment agent of one embodiment of the present invention, particles which pass through 80 mesh (177 μm) are included in an amount of preferably 90% or more and more preferably 93% or more.

Here, the "average particle diameter" in the present description means an average value obtained by optionally selecting the statistically reliable number of particles, measuring the longest particle size of each particle with a microscope, and arithmetically averaging the values. The "average particle diameter" described in the present description has the same definition. It should be noted that particles may be appropriately put through e.g. a sieve to obtain a desired average particle diameter.

The granular water-soluble lubricant in the treatment agent of one embodiment of the present invention (when two or more lubricants are selected, the total amount thereof) is included in an agent A in an amount of preferably 0.01 to 50.0 mass %, more preferably 0.1 to 40.0 mass %, further preferably 1.0 to 30.0 mass %, still further preferably 2.0 to 20.0 mass %, still further preferably 3.0 to 15.0 mass %, still further preferably 5.0 to 10.0 mass %, and still further preferably 6.0 to 7.0 mass %. According to this embodiment, gel has a moderate viscosity. In particular when the granular water-soluble lubricant is included in an amount of 5.0 mass % or more, the expected technical effect can be efficiently shown.

Here, the "moderate viscosity" is, in plain words, the viscosity at which gel evenly adheres to the whole pouch wall surface and the gel hardly falls even when the outlet faces down (that is, a pool of liquid (gel) derived from an excess of the treatment agent does not develop around the outlet), and on the other hand, when feces get into the inside of the pouch, feces adhere to the gel on the wall surface and simultaneously fall, and feces are smoothly discharged with the gel when the outlet is opened.

The granular water-soluble lubricant in the treatment agent of one embodiment of the present invention preferably has gelation ability. The viscosity at the time of gelation is also not particularly restricted; however, the viscosity when adding 1 g of a granular water-soluble lubricant to 100 g of water (water temperature 25° C.), stirring the obtained mixture for 2 minutes and leaving the mixture to stand for 60 minutes is preferably about 2000 to 20000 mPa·s, more preferably about 5000 to 18000 mPa·s, and further preferably about 7000 to 16000 mPa·s, and may be about 7000 to 15000 mPa·s, about 7000 to 12000 mPa·s, and about 7000 to 10000 mPa·s. It should be noted that as the value of viscosity a value measured at a gel temperature of 25° C. by a B-type viscometer is used in the present description.

(Water-Soluble Carboxymethyl Cellulose)

According to a preferred embodiment of the present invention, the granular water-soluble lubricant is water-soluble carboxymethyl cellulose. According to this embodiment, gel has a moderate viscosity.

As the method for preparing water-soluble carboxymethyl cellulose, a commercial product may be purchased, and examples thereof include trade name SUNROSE (registered trademark) F1400MG from NIPPON PAPER Chemicals CO., LTD. and the like.

(Carboxyvinyl Polymer (What is Called Carbomer))

According to a preferred embodiment of the present invention, the granular water-soluble lubricant is a carboxyvinyl polymer (what is called carbomer). The carboxyvinyl polymer is an acrylic acid-based cross-linked copolymer. In addition, this carboxyvinyl polymer may be a carboxyvinyl polymer salt. Carboxyvinyl polymers have affinity for water, and is mixed with water in a basic region (above pH 7, preferably pH 9 to 11) to become a highly viscous material in the form of gel. Carbomer itself is commonly acid; however, when being mixed with water, the treatment agent of one embodiment of the present invention is neutralized with e.g. sodium bicarbonate and slaked lime and has about pH 9 to 11. Accordingly, when a carboxyvinyl polymer is included in the treatment agent, the viscosity of the treatment agent increases. In a preferred embodiment of the present invention, carbomer is mixed with water to become a highly viscous material in the form of gel, and the viscosity at a concentration of 0.5% and 25° C. is 5400 to 70000 mPa·s. In a preferred embodiment of the present invention, the feces treatment agent for colostomy would become a highly viscous material in the form of gel by mixing with water under the condition of pH 9 to 11, and the viscosity at a concentration of 0.5% and 25° C. is 5400 to 70000 mPa·s.

The carbomer can be freely selected from commercial products; however, one which has little change in viscosity over time and is highly stable is preferably used. Examples of commercial products of carboxyvinyl polymers can include product name: AQUPEC (registered trademark) HV-505 manufactured by Sumitomo Seika Chemicals Company, Limited. and the like.

(Bentonite)

According to a preferred embodiment of the present invention, the granular water-soluble lubricant is bentonite. Bentonite includes lots of aluminum phyllosilicate in the form of layer, and has properties such as high viscous properties, adhesive properties, water-absorbing properties and adsorptive properties.

Bentonite can be freely selected from commercial products. Examples of commercial products of bentonite can include KUNIMINE F, MOISTNITE (registered trademark) S, MOISTNITE (registered trademark) U manufactured by KUNIMINE INDUSTRIES CO., LTD., 250SA-B from HOYO Bentonite Mining Co., Ltd. and the like.

(2) Granular Water-Absorbing Gelling Agent

The treatment agent of one embodiment of the present invention includes an agent A, and the agent A includes a granular water-absorbing gelling agent as the component (2). When a granular water-absorbing gelling agent is included, a time until the treatment agent gels can be made earlier.

As the granular water-absorbing gelling agent, polyacrylic acid or a salt thereof is preferred. As the salt, a sodium salt is preferred. In addition, as the granular water-absorbing gelling agent, a cross-linked acrylic acid and sodium acrylate copolymer is preferred. In addition, the cross-linked acrylic acid and sodium acrylate copolymer preferably has a tridimensionally crosslinked molecular structure. That is, it is preferred that the cross-linked acrylic acid and sodium acrylate copolymer be based on an acrylic acid salt (a cross-linked acrylic acid and sodium acrylate copolymer) and have a tridimensionally crosslinked molecular structure.

According to a preferred embodiment of the present invention, the average particle diameter of a granular water-absorbing gelling agent is preferably 1 to 106 μm, more preferably 20 to 60 μm, further preferably 22 to 50 μm, still further preferably 24 to 40 μm, and still further preferably 26 to 35 μm. The viscosity remarkably increases by contact with water because of the significantly small particle size as described above.

According to a preferred embodiment of the present invention, the granular water-absorbing gelling agent includes particles with a particle size of 106 μm or less in an amount of preferably 95.0 mass % or more and more preferably 99.0 mass % or more. In addition, according to a preferred embodiment of the present invention, the granular water-absorbing gelling agent includes particles with a particle size of 53 μm or less in an amount of preferably 85.0 mass % or more and more preferably 90.0 mass % or more. In addition, according to a preferred embodiment of the present invention, the granular water-absorbing gelling agent includes particles with a particle size of 20 μm or less in an amount of preferably 18.0 mass % or more and more preferably 20.0 mass % or more. On the other hand, according to a preferred embodiment of the present invention, the granular water-absorbing gelling agent includes particles with a particle size of 5 μm or less in an amount of up to preferably 10.0 mass % or less, more preferably 8.0 mass % or less, and further preferably 5.0 mass % or less.

According to a preferred embodiment of the present invention, the granular water-soluble lubricant has gelation ability, and the onset of gelation of the granular water-absorbing gelling agent is earlier than the onset of gelation of the granular water-soluble lubricant. In addition, according to a preferred embodiment of the present invention, the granular water-absorbing gelling agent is a water-absorbing polymer which starts gelling within a minute, preferably within 30 seconds, more preferably within 20 seconds, and further preferably within 10 seconds. The lower limit is commonly about 20 seconds, but not restricted thereto. In addition, according to a preferred embodiment of the present invention, the granular water-soluble lubricant starts gelling within 20 minutes, preferably within 15 minutes, more preferably within 10 minutes, and further preferably within 5 minutes. The lower limit is commonly about 180 seconds, but not restricted thereto. It is thought that these embodiments have the following action effects. That is, because there is a difference in the onset time of gelation between the granular water-soluble lubricant and granular water-absorbing gelling agent, a time until gelation by the action of the granular water-absorbing gelling agent is shortened, and the granular water-soluble lubricant starts gelling after a predetermined time has passed. Accordingly, gelation can be retained for a prolonged time. From the viewpoint, characteristics required as a lubricant can be shown.

The viscosity when the granular water-absorbing gelling agent gels is also not particularly restricted; however, the viscosity when adding 1 g of a granular water-absorbing gelling agent to 100 g of water (water temperature 25° C.), stirring the obtained mixture for a minute, and leaving the mixture to stand for 5 minutes is preferably about 2000 to 15000 mPa·s, more preferably about 3000 to 14000 mPa·s, and further preferably about 5000 to 12000 mPa·s.

The granular water-absorbing gelling agent (when two or more agents are selected, the total amount thereof) is included in an agent A in an amount of preferably 0.1 to 70.0 mass %, more preferably 5.0 to 50.0 mass %, further preferably 10.0 to 40.0 mass %, still further preferably 5.0 to 30.0 mass %, still further preferably 10.0 to 28.0 mass %, still further preferably 15.0 to 25.0 mass %, and still further preferably 16.0 to 20.0 mass %. In this range, gel has a moderate viscosity.

As a method for preparing a granular water-absorbing gelling agent, a commercial product may be purchased, and, for example, SANFRESH (registered trademark) ST-500MPSA manufactured by Sanyo chemical Industries, Ltd. is suitable. Because SANFRESH (registered trademark) ST-500MPSA has a significantly small particle size, the viscosity remarkably increases by contact with water. SANFRESH is based on an acrylic acid salt (a cross-linked acrylic acid and sodium acrylate copolymer) and has a tridimensionally crosslinked molecular structure. When this is brought into contact with water, the carboxyl groups are ionized and the molecular chain with increased hydrophilicity expands to dissolve in water. Simultaneously, water gets into a gap of the molecular chain due to an osmotic pressure generated by a difference in ion concentration, and also the molecular chain expands to a region restricted by three dimensional cross-linking due to a repelling force of minus ions. And, a state in which water is incorporated into each mesh of an expanded fishnet is obtained. As described above, a water-absorbing power is expressed by the action that the molecular chain expands to dissolve in water, and the action that an expansion of the molecular chain is restricted by a cross-linked structure.

(3) Sodium Bicarbonate

The treatment agent of one embodiment of the present invention includes an agent A, and the agent A includes sodium bicarbonate as the component (3). There is a technical effect to inhibit gel from curing by including sodium bicarbonate. A mechanism to show the technical effect is not restricted; however, it is thought that this is because the solidification of a granular water-absorbing gelling agent is moderately inhibited. Sodium bicarbonate (sodium hydrogen carbonate) is a hydrogen carbonate of sodium represented by the composition formula $NaHCO_3$. Sodium bicarbonate can be used as a food additive and is safe for the human body. Therefore, sodium bicarbonate is suitable also because a chemical burn is not easily caused. In addition, sodium bicarbonate can be directly drained into waste water, and posttreatment is very easy. As a method for preparing sodium bicarbonate, a commercial product can be purchased, and, for example, industrial grade sodium bicarbonate manufactured by Tosoh Corporation, QINDAO HAIWAN GROUP IMP. & EXP. CO. and Zichuan Antou Alum Factory, and the like are preferred.

The average particle diameter of sodium bicarbonate is also not particularly restricted, and is preferably 30 to 150 μm and more preferably 80 to 100 μm.

Sodium bicarbonate is included in an agent A in an amount of preferably 10.0 to 95.0 mass %, more preferably 30.0 to 90.0 mass %, further preferably 40.0 to 80.0 mass %, still further preferably 50.0 to 70.0 mass %, and still further preferably 56.5 to 65.0 mass %. This embodiment has the technical effect of decomposing and adsorbing sulfur compounds and fatty acid compounds, which are bad smell components in stool. In particular, when sodium bicarbonate is included in an amount of 56.5 mass % or more, the expected technical effect can be further shown.

(4) Zinc Oxide, Limonite and Zinc Sulfide

The treatment agent of one embodiment of the present invention includes an agent A, and the agent A includes as the component (4) a component including at least one selected from the group consisting of zinc oxide, limonite and zinc sulfide. It is epochal to find that the component (4) has the action of greatly contributing to the gelation ability of the treatment agent.

The average particle diameter (D50) of the component (4) is also not particularly restricted, and is preferably 0.1 to 200 μm, more preferably 0.2 to 110 μm, further preferably 0.3 to 100 μm, still further preferably 0.4 to 50 μm, still further preferably 0.5 to 25 μm, still further preferably 0.5 to 10 μm, still further preferably 0.5 to 5 μm, and still further preferably 0.5 to 1 μm. Here, D50 is a cumulative 50% particle diameter based on particle size distribution on a volumetric basis. D50 can be measured using a commercially available particle size measuring device. This particle size measuring device may be based on any means such as a dynamic light scattering method, a laser diffraction method, a laser scattering method, or a pore electrical resistance method.

The component (4) (when two or more components are selected, the total amount thereof) is included in an agent A in an amount of preferably 0.1 to 80.0 mass %, more preferably 1.0 to 70.0 mass %, further preferably 3.0 to 60.0 mass %, still further preferably 5.0 to 50.0 mass %, still further preferably 5.0 to 30.0 mass %, still further preferably 10.0 to 20.0 mass %, and more preferably 15.0 to 17.0 mass %. Therefore, according to a preferred embodiment of the present invention, the component (4) is included in an agent A in an amount of 10.0 to 20.0 mass %. This embodiment has the technical effect of decomposing and adsorbing sulfur compounds and fatty acid compounds, which are bad smell components in stool.

(Zinc Oxide)

Zinc oxide is an oxide of zinc represented by ZnO, and has the effect of deodorization and odor removal by adsorbing odor components such as ammonia and sulfide.

Zinc oxide can be freely selected from commercial products. Examples thereof include zinc oxide I (manufactured by HakusuiTech Co., Ltd.), zinc oxide II (manufactured by HakusuiTech Co., Ltd.) and the like.

(Limonite)

The chemical composition of limonite is $FeO(OH).nH_2O$, and hematite ($Fe_2O_3$), clay mineral, manganese oxide (II) and the like may be included as impurities, in some cases. The technical effect of decomposing and adsorbing sulfur compounds and fatty acid compounds, which are bad smell components in stool, is obtained by including limonite.

Limonite can be freely selected from commercial products. Examples thereof include A. S. O (manufactured by JAPAN LIMONITE Co., Ltd.), that manufactured by LMB50, and the like.

(Zinc Sulfide)

Zinc sulfide is a covalently binding compound represented by the composition formula ZnS, and is a white or yellow powder or crystal.

Zinc sulfide can be freely selected from commercial products. Examples thereof include RAK series manufactured by SAKAI CHEMICAL INDUSTRY CO., LTD. and the like.

(Water-Soluble Base Material)

In the treatment agent of one embodiment of the present invention, an agent A is contained in a water-soluble base material. In the treatment agent of one embodiment of the present invention, an agent A is sealed in a water-soluble base material.

The water-soluble base material is not particularly restricted as long as it is a base material which is dissolved in water. Examples thereof include a water-soluble paper, a water-soluble film and the like. The form of the water-soluble base material is also not particularly restricted; however, it is preferably in the form of pouch. In an embodiment of the present invention, an agent A is contained (preferably, sealed) in a pouched water-soluble base material in the feces treatment agent for colostomy. The water-soluble base material has a function as a pouch (exterior package) for an agent A, and also a function as a part of the feces treatment agent for colostomy because this water-soluble base material itself contributes to gelation by contact with water. In addition, the treatment agent of one embodiment of the present invention has a function of gelation by subsequent contact with water, and the technical idea of the present application formed by allowing these functions to act in cooperation has not been present until now.

The size of the water-soluble base material is not particularly restricted; however, it is preferably a size which can be put into the outlet of a pouch. In addition, the form of the size of the water-soluble base material is also not particularly restricted as long as it is preferably in a form which can be put into the outlet of a pouch. Because the size of the outlet of a commercially available pouch is at most about 7 cm or less, about 6 cm or less or about 5 cm or less, the size of the water-soluble base material is preferably smaller than the size of the outlet of a pouch. Therefore, the greatest width of the water-soluble base material is preferably less than 7 cm, 6 cm, 5 cm or 3 cm.

(5) Lignin, Slaked Lime and Limestone

The treatment agent of one embodiment of the present invention includes an agent A, and the agent A preferably further includes as the component (5) a component including at least one selected from the group consisting of lignin, slaked lime and limestone. Therefore, according to a preferred embodiment of the present invention, the component (5) including at least one selected from the group consisting of lignin, slaked lime and limestone is further included. According to this embodiment, a deodorant effect is improved. In addition, the action of eliminating bacteria, and the technical effect of decomposing and adsorbing sulfur compounds and fatty acid compounds, which are bad smell components in stool, are obtained.

The average particle diameter of the component (5) is also not particularly restricted, and is preferably 0.1 to 1000 μm, more preferably 10 to 150 μm, and further preferably 30 to 50 μm. In this range, the effect of decomposing and adsorbing bad smell components in stool, is obtained. In addition, particles which pass through 100 mesh (150 μm) are included in an amount of preferably 90% or more and more preferably 93% or more.

The component (5) (when two or more components are selected, the total amount thereof) is included in an agent A in an amount of preferably 0.01 to 30.0 mass %, more preferably 0.1 to 20.0 mass %, further preferably 0.5 to 10.0 mass %, and still further preferably 1.0 to 5.0 mass %. In this range, the effect of decomposing and adsorbing bad smell components in stool is obtained.

(Lignin)

Lignin is a high molecular phenolic compound, which is involved in lignification of higher plants, and is also called a woody element.

Lignin can be freely selected from commercial products. Examples thereof include SAN X and VANILLEX manufactured by NIPPON PAPER Chemicals CO., LTD., that manufactured by PEARLLEX, and the like.

(Slaked Lime)

Slaked lime ($Ca(OH)_2$) is strong alkali, and thus a sterilizing effect on feces (excreta, particularly stool) is considerable.

The shape of slaked lime is not particularly restricted, and for example a granular shape, a pellet shape and the like can be exemplified. However, a granular shape is preferred from the viewpoint that slaked lime is effectively dispersed in stool.

Slaked lime may be one which is surface-treated with a hydrophobic coating agent. In addition, slaked lime may be synthesized or a commercial product may be used.

As the method for preparing slaked lime, a method by purchasing a commercial product is preferred, and, for example, one from Ube Material Industries, Ltd. and the like are preferred.

(Limestone)

Limestone (calcium carbonate) is a carbonate of calcium represented by the composition formula $CaCO_3$. Limestone is alkaline and thus has the same effects as of slaked lime.

The form of limestone is not particularly restricted, and for example a granular form, a pellet form and the like can be exemplified. However, a granular form is preferred from the viewpoint that limestone is effectively dispersed in stool.

As the method for preparing limestone, a method by purchasing a commercial product is preferred, and, for example, calcium carbonate from Ube Material Industries, Ltd., and calcium carbonate for industrial use from Yoshizawa Lime Industry CO., LTD., and the like are preferred.

According to a preferred embodiment of the present invention, the component (4) is zinc oxide or zinc sulfide, and the component (5) is slaked lime or limestone. This embodiment has a technical effect that a treatment agent turns white. Here, stoma patients sometimes have concerns which heathy people have never imagined in daily lives. For example, female people want to wear a white blouse in many cases, and male people have many opportunities to wear a white shirt. However, when stoma patients fail in discharging excreta from a pouch and adding a lubricant, feces adhere to clothes, which is noticeable. On the contrary, according to this embodiment, this problem can be solved by the technical effect that a treatment agent turns white.

It should be noted that according to a preferred embodiment of the present invention, the treatment agent does not substantially include water. In addition, according to a preferred embodiment of the present invention, the treatment agent does not include water. According to this embodiment, it is not required to carry a lubricant including a liquid accounting for most of its weight on a constant basis, and portability is dramatically improved. This technical idea that a treatment agent not including e.g. water is allowed to subsequently gel has not been present until now, which is epochal. Here, substantially not including water means that the treatment agent does not include moisture other than moisture in air.

(Viscosity of Feces Treatment Agent for Colostomy)

The viscosity of the treatment agent of one embodiment of the present invention does not depend on only the viscous properties of the (2) granular water-absorbing gelling agent alone or the viscous properties of the (1) granular water-soluble lubricant alone, and can be decided by interaction of the components (1) to (4). Here, as the viscosity of the treatment agent of one embodiment of the present invention, the viscosity obtained by adding 1 g of a treatment agent to 10 g of water (water temperature 25° C.), stirring the obtained mixture for a minute, and leaving the mixture to stand for an hour is preferably about 2000 to 15000 mPa·s, more preferably about 3000 to 14000 mPa·s, and further preferably about 5000 to 12000 mPa·s. In this range, gel is not too hard or too soft, the development of undissolved lumps can be also inhibited, and discharge properties are also significantly improved.

(Method for Producing Feces Treatment Agent for Colostomy)

The method for producing a treatment agent of one embodiment of the present invention has containing an agent A including (1) a granular water-soluble lubricant, (2) a granular water-absorbing gelling agent, (3) sodium bicarbonate, and (4) a component including at least one selected from the group consisting of zinc oxide, limonite and zinc sulfide in a water-soluble base material.

In an embodiment in which a treatment agent is produced using a water-soluble paper as the water-soluble base material, it is only needed to create the water-soluble paper in the form of pouch, add an agent A to this pouched water-soluble paper, and seal the pouched water-soluble paper by a known method so that the agent A is not leaked. It should be noted that an agent A may be created in advance before adding (1) a granular water-soluble lubricant, (2) a granular water-absorbing gelling agent, (3) sodium bicarbonate, and (4) a component including at least one selected from the group consisting of zinc oxide, limonite and zinc sulfide to the pouched water-soluble paper, or an agent A may be created in the pouched water-soluble paper by adding (1) a granular water-soluble lubricant, (2) a granular water-absorbing gelling agent, (3) sodium bicarbonate, and (4) a component including at least one selected from the group consisting of zinc oxide, limonite and zinc sulfide to the pouched water-soluble paper. The method for producing a treatment agent of one embodiment of the present invention has a technical effect that the amount of agent A included can be increased by using a pouched water-soluble paper.

In an embodiment in which a treatment agent is produced using a water-soluble film as the water-soluble base material, an agent A may be contained in the water-soluble film by a processing technique such as pressure bonding. However, the amount of agent A which can be contained in the water-soluble film is restricted (it is preferred to include a constant amount of agent to treat feces), and accordingly it is preferred that a water-soluble paper be used as the water-soluble base material.

As described above, a treatment agent in which an agent A is contained in a water-soluble base material can be created.

(Method for Using Feces Treatment Agent for Colostomy)

The method for using a treatment agent will be described. Because the treatment agent of one embodiment of the present invention has a size which can be added from e.g. the outlet of a colostomy pouch, the treatment agent can be used for any colostomy pouches. In an embodiment of the present invention, a treatment agent having a pouched water-soluble base material in which an agent A is contained is put into a colostomy pouch without taking out the agent A of the water-soluble base material with the agent A contained in the water-soluble base material. According to the present embodiment, the pouched water-soluble base material has a function as an exterior package material for an agent A and a function as a component forming the treatment agent. In an embodiment of the present invention, a treatment agent having an agent A contained in a pouched water-soluble base material has a technical effect that separate exterior package materials are not required.

FIG. 1 is a schematic perspective view which shows an example of a colostomy pouch. As shown in FIG. 1, a colostomy pouch 10 is equipped with a back surface of the colostomy pouch 11, a surface of the colostomy pouch 12, a flange 14 which can be removed from and attached to the stoma portion, a gas releasing portion 15, an outlet 16 to discharge feces, and a stop portion 13 to prevent feces from being discharged until the time of need. It should be noted that the colostomy pouch in FIG. 1 is what is called a two-piece device; however, it is not necessary to say that the treatment agent of one embodiment of the present invention can be also used for a colostomy pouch of a one-piece device. Needless to say, the treatment agent of one embodiment of the present invention can be also applied to other forms of colostomy pouch.

FIG. 2 is a schematic view, in which a stoma patient attaching a colostomy pouch opens the outlet with one hand and adds a treatment agent from the outlet with another hand. As shown in FIG. 2, while opening the outlet 16 of the colostomy pouch 10 with a left hand 102, the stoma patient attaching the colostomy pouch 10 adds a treatment agent 20, in which an agent A is contained in a water-soluble base material, with a right hand 103. As described above, according to the present invention, operativity when adding a treatment agent is dramatically improved. Furthermore, after adding the treatment agent 20, it is only needed to prepare water in advance in e.g. a toilet, open the outlet 16 with the left hand 102, and add water with the right hand 103.

Incidentally, stoma patients are not revealed by their appearances to be stoma patients. Therefore, when using e.g. a multipurpose toilet (toilet for people with disabilities), for example, a person with a disability waits for the multipurpose toilet with a look of annoyance in some cases particularly when the time to use the toilet is long. On the contrary, in the treatment agent of one embodiment of the present invention, operativity is improved and a time for gelation is also short, and thus the time to use a multipurpose toilet (toilet for people with disabilities) can be also shortened. Accordingly, the situation described above is not produced. In addition, for example, some patients hiding the use of a stoma at the office or the like exist. In this case, the patients cannot carry a bottle-type lubricant to a toilet because the size is large. In addition, when using a lubricant packet, divided into small amounts, both hands are required to squeeze a lubricant from the packet and it is inconvenient to open the outlet of a colostomy pouch. In the case of operativity as described above, unnecessary time is required for a toilet. When the time for a toilet at the office is excessively long each time, although the patients only excrete excreta from a pouch and add a lubricant, the patients can be pointed out as being lazy. On the contrary, when using the treatment agent of one embodiment of the present invention, it is not required to carry a large bottle-type lubricant to a toilet, and it is also not required to squeeze a lubricant from a packet, and accordingly the treatment agent of one embodiment of the present invention can be suitably used also in the situation as described above. In addition, because it is possible to add a treatment agent without feeling rushed, a failure of adherence of excreta to clothes can be also reduced. In addition, because operativity is also improved, a failure of adherence of excreta to clothes can be also reduced. In addition, the treatment agent of one embodiment of the present invention can be easily put in a small handbag as carried by female people, and can be also easily put in a pocket of men's pants (it is difficult to put a bottle-type lubricant therein).

In an embodiment of the present invention, the mass of the treatment agent put into a colostomy pouch is not particularly restricted, and is preferably 1 to 10 g, more preferably 2 to 8 g, and further preferably 4 to 7 g. Because it is light as described above, portability is remarkably improved.

(Kit of Feces Treatment Agent for Colostomy)

According to one embodiment of the present invention, there is also provided a kit of a feces treatment agent for colostomy, including the above treatment agent and a container to contain water. Water can be easily added from the outlet of a colostomy pouch by combining the container to contain water. According to a preferred embodiment of the present invention, the amount of water suitable for the weight of the treatment agent can be easily taken. For example, the container may be a container, in which the amount of water to fill the container is an amount suitable for the weight of a treatment agent, or a container with a scale to show the amount of water suitable for the weight of a treatment agent.

(Method for Treating Feces in Colostomy Pouch)

According to the present invention, there is also provided a method for treating feces in a colostomy pouch by separately adding the above treatment agent and water to the colostomy pouch. By this configuration, in other words, it is not required to carry a lubricant including a liquid or gel accounting for most of its weight on a constant basis, and portability is dramatically improved. That is, the weight which users carry is only about ½0 to ½0, and accordingly portability is dramatically improved. It should be noted that the amount of water is not restricted, and is preferably about 2 to 20 times, more preferably about 3 to 15 times, and preferably 4 to 10 times the total mass of the treatment agent. In the amount as described above, a proper viscosity can be provided to gel.

EXAMPLES

The present invention will now be further described by showing typical embodiments of the present invention. Needless to say, however, the present invention is not limited to these embodiments. It should be noted that unless otherwise noticed in Examples, "parts" represent "parts by mass" and "%" represents "mass %." In addition, unless otherwise specified, operations and the measurement of e.g. physical properties are measured under the condition of room temperature (20 to 25° C.)/a relative humidity of 40 to 50% RH.

Example 1

Into a water-soluble base material (0.3 g) having a water-soluble paper whose one surface was laminated with PVA, an agent A obtained by mixing a granular water-soluble lubricant (CMC), a granular water-absorbing gelling agent (water-absorbing polymer), sodium bicarbonate and zinc oxide with composition shown in Table 1 was added, and the water-soluble base material was sealed with heat (130° C.) at a heat sealing pressure of 2 kg/cm$^2$ for a second to create a feces treatment agent for colostomy in which the agent A is contained in the water-soluble base material (size: 7 cm (including a margin for glue)×greatest width: 2.5 cm (including a margin for glue)).

After that, (1) While the outlet of the colostomy pouch was opened with one hand, the feces treatment agent for colostomy created above was added from the outlet of the colostomy pouch with another hand.

(2) Subsequently, while the outlet of the colostomy pouch was opened with one hand, all water was poured from the container which contains 50 g of water with another hand.

(3) Then, the gelled feces treatment agent for colostomy was spread to the whole inner wall of the pouch by rubbing and kneading both the walls of the colostomy pouch with both hands.

(4) After that, the colostomy pouch was hanged with an s-hook and left to stand for an hour.

(5) After that, 160 g of stool was added from an opening portion provided on the center of the flange in the colostomy pouch.

Examples 2 to 4, Comparative Examples 1 to 6

The experiment was carried out in the same manner as in Example 1 except that components and the like were changed as shown in Table 1. It should be noted that "-" in Table 1 indicates that a corresponding component was not added.

[Evaluation]

<Gelation Ability in Pouch>

The gelation ability in a pouch was evaluated.

○: After the (2) above, it was verified that a feces treatment agent for colostomy gelled within 3 minutes.

×: After the (2) above, a feces treatment agent for colostomy required 60 minutes or more to gel.

−: Gelation did not occur.

<Viscous Properties in Pouch>

The viscous properties of a feces treatment agent for colostomy in a pouch were evaluated.

⊙: After leaving a pouch to stand for an hour in the (4) above, gel evenly adhered to the whole pouch wall surface.

Δ: After leaving a pouch to stand for an hour in the (4) above, it was verified that gel ran down the wall surface.

x: Even when a feces treatment agent for colostomy was spread on the whole pouch wall surface in the (3) above, gel was too hard and unevenly adhered to the pouch wall surface.

–: An agent was watery and did not gel.

<Existence of Undissolved Lumps>

The occurrence of undissolved lumps (a portion which remains powder and solidifies) in a pouch was visually verified.

No: after leaving a pouch to stand for an hour in the (4) above, undissolved lumps were not visually verified.

Yes: after leaving a pouch to stand for an hour in the (4) above, a proportion that the development of undissolved lumps was visually verified was shown by vol % to the whole gel. It should be noted that the undissolved lump means a lump with a diameter of 0.5 cm or more.

<Discharge Properties>

Stool was added, and the stool discharge properties from the outlet of a colostomy pouch were evaluated.

⊙: When the outlet was opened 11 hours after adding stool in the (5) above, stool was smoothly discharged by gravity, o: After the outlet was opened 11 hours after adding stool in the (5) above, stool was smoothly discharged with hands, and x: After the outlet was opened 11 hours after adding stool in the (5) above, stool was not smoothly discharged even when using hands.

<Odor>

The odor evaluation is an evaluation of the odor felt during discharging stool.

⊙: The odor is hardly felt, o: The odor is slightly felt, and x: The odor is felt.

<Adherence in all Directions>

After discharging stool, the proportion of residues (gel and stool) adhering to the pouch wall surface was shown.

o: The residues (gel and stool) adhering to the pouch wall surface are about 2% of the whole area of the wall surface, Δ: The residues (gel and stool) adhering to the pouch wall surface are about 5% of the whole area of the wall surface, x: The residues (gel and stool) adhering to the pouch wall surface are about 10% of the whole area of the wall surface, and xx: The residues (gel and stool) adhering to the pouch wall surface are about 20% of the whole area of the wall surface.

<Evaluation of Onset Time of Gelation of Granular Water-Soluble Lubricant and Granular Water-Absorbing Gelling Agent>

To 100 ml of water, 1 g of a granular water-soluble lubricant was added, and the obtained mixture was left to stand without stirring.

To 100 ml of water, 1 mg of a granular water-absorbing gelling agent was added, and the obtained mixture was left to stand without stirring.

The granular water-soluble lubricant became the form of gel after 10 minutes, and thus evaluated as gelation within 10 minutes. The granular water-absorbing gelling agent became the form of gel after a minute, and thus evaluated as gelation within a minute.

Therefore, it was verified that the onset of gelation of the granular water-absorbing gelling agent was earlier than the onset of gelation of the granular water-soluble lubricant.

TABLE 1

|  | Amount of stool | Water | (1) Water-soluble lubricant cmc | (2) Granular water-absorbing gelling agent | (3) Sodium bicarbonate | (4) Zinc oxide | (5) Slaked lime (g) |
|---|---|---|---|---|---|---|---|
| Example 1 (Treatment agent 5.9 g) | 160 g | 50 g | 6.8% | 17.0% | 59.3% | 16.9% | — |
| Example 2 (Treatment agent 6.2 g) | 160 g | 50 g | 6.4% | 19.4% | 56.5% | 16.1% | 1.6% |
| Example 3 (Treatment agent 5.4 g) | 160 g | 50 g | 7.4% | 18.5% | 55.6% | 18.5% | — |
| Example 4 (Treatment agent 5.7 g) | 160 g | 50 g | 3.6% | 17.5% | 61.4% | 17.5% | — |
| Comparative Example 1 (Treatment agent 5.9 g) | 160 g | 50 g | 23.7% | — | 59.4% | 16.9% | — |
| Comparative Example 2 (Treatment agent 5.9 g) | 160 g | 50 g | — | 23.7% | 59.4% | 16.9% | — |
| Comparative Example 3 (Treatment agent 4.9 g) | 160 g | 50 g | 8.2% | 20.4% | 71.4% | — | — |
| Comparative Example 4 (Treatment agent 2.4 g) | 160 g | 50 g | 16.6% | 41.7% | — | 41.7% | — |
| Comparative Example 5 (Treatment agent 2.7 g) | 160 g | 50 g | 14.8% | 44.5% | — | 37.0% | 3.7% |
| Comparative Example 6 (Treatment agent 5.2 g) | 160 g | 50 g | 7.7% | 23.1% | 67.3% | — | 1.9% |

|  | Gelation ability | Viscous property | Undissolved lump | Discharge property | Odor | Adhesion in all directions |
|---|---|---|---|---|---|---|
| Example 1 (Treatment agent 5.9 g) | o | o | No | ⊙ | o | o |
| Example 2 (Treatment agent 6.2 g) | o | o | No | ⊙ | ⊙ | o |
| Example 3 (Treatment agent 5.4 g) | o | o | About 5 vol % | ⊙ | o | Δ |

TABLE 1-continued

| | | | | | | |
|---|---|---|---|---|---|---|
| Example 4 (Treatment agent 5.7 g) | ○ | △ | No | ◎ | ○ | ○ |
| Comparative Example 1 (Treatment agent 5.9 g) | X | ○ | No | ◎ | ○ | ○ |
| Comparative Example 2 (Treatment agent 5.9 g) | ○ | X | About 40 vol % | X | X | X |
| Comparative Example 3 (Treatment agent 4.9 g) | — | — | No | ◎ | X | ○ |
| Comparative Example 4 (Treatment agent 2.4 g) | ○ | X | About 40 vol % | X | X | XX |
| Comparative Example 5 (Treatment agent 2.7 g) | ○ | X | About 20 vol % | ○ | X | X |
| Comparative Example 6 (Treatment agent 5.2 g) | — | — | No | ◎ | ○ | ○ |

(1) CMC (carboxymethy cellulose) trade name SUNROSE (registered trademark) F1400MG from NIPPON PAPER Chemicals CO., LTD., average particle diameter: 80 mesh (passing through under 177 μm),
(2) Granular water-absorbing gelling agent: SANFRESH ST-500MPSA) from Sanyo Chemical Industries, Ltd., average particle diameter: 30 μm (particle size 106 μm or less: 99.3%, particle size 53 μm or less: 90.3%, particle size 20 μm or less: 22.5%, particle size 5 μm or less: MAX 5%),
(3) Sodium bicarbonate: manufactured by Tosoh Corporation, average particle diameter: 90 μm
(4) Zinc oxide I: manufactured by HakusuiTech Co., Ltd., average particle diameter: 0.6 μm, and
(5) Slaked lime: manufactured by Ube Material Industries, Ltd., average particle diameter: 95% passing through 100 mesh (150 μm or less).

<Consideration>

In experiments using the feces treatment agents for colostomy in Examples 1 to 4, all evaluation items were good. In particular, in the present experiment, it is notable that the results were good even when using normal stool (stool which does not include an excess of moisture). That is, stool of stoma patients include much moisture, and thus there is a tendency that discharge properties are better than those of normal stool. That is, if discharge properties in normal stool, which is more difficult to discharge, are good, discharge properties in stool of stoma patients will be also good.

When considering the results in detail, all evaluation items were particularly good in Examples 1 and 2.

Example 2 is suitable because an odor removing effect is high by using slaked lime.

On the other hand,

Example 1 is suitable because slaked lime is not used and irritation to the skin of users is reduced.

In Example 3, because the amount of sodium bicarbonate included was slightly small, gel became hard, the development of undissolved lumps was slightly verified, and adherence in all directions was also verified. However, there was not an influence on discharge properties and odor removal properties, and Example 3 had characteristics required as a lubricant.

In Example 4, because the amount of granular water-soluble lubricant included was slightly small, gel became soft. However, there was not an influence on discharge properties and odor removal properties, and Example 4 had characteristics required as a lubricant.

On the other hand, in Comparative Example 1, because a granular water-absorbing gelling agent was not added, a time until becoming the form of gel was slow, and Comparative Example 1 did not have characteristics required as a lubricant.

In Comparative Example 2, because a granular water-soluble lubricant was not added, many undissolved lumps developed. That is, because gel was localized (dispersibility was bad) and unevenly brought into contact with stool, discharge properties were bad, the odor at the time of discharging was strong, and much adhesion in all directions was observed.

Comparative Example 3 did not include the component (4), become the form of gel, and have characteristics required as a lubricant.

In Comparative Example 4, because sodium bicarbonate was not added, many undissolved lumps developed. That is, because gel was localized (dispersibility was bad) and unevenly brought into contact with stool, discharge properties were bad, the odor at the time of discharging was strong, and much adhesion in all directions was observed. Here, the reason why the result of adhesion in all directions was "xx" will be surmised. In Comparative Example 2, because a water-soluble lubricant (CMC) was not contained and only a granular water-absorbing gelling agent was contained, gel became hard. On the other hand, it is thought that sodium bicarbonate shows a reaction which moderately inhibits the solidification of a granular water-absorbing gelling agent. However, because sodium bicarbonate is not included in Comparative Example 4, gel became hard. Because gel became hard in both Comparative Example 2 and Comparative Example 4, adhesion in all directions increased. However, because the viscosity in Comparative Example 4 was lower, lubricity was worse in Comparative Example 4. Accordingly it is supposed that the results in Comparative Example 4 were worse.

In Comparative Example 5, slaked lime is also added, and odor removal properties are expected. However, because sodium bicarbonate is not added, many undissolved lumps developed, gel was localized (dispersibility was bad) and unevenly brought into contact with stool. Accordingly, the odor at the time of discharging was strong.

Comparative Example 6 did not include the component (4), become the form of gel and have characteristics required as a lubricant. However, unlike Comparative Example 3, the result of odor was good because slaked lime is included.

It should be noted that the present application is based on Japanese Patent Application No. 2017-006065 filed on Jan. 17, 2017, and the disclosed contents are incorporated by reference in its entirety.

REFERENCE SIGNS LIST

10: colostomy pouch
11: back surface of colostomy pouch
12: surface of colostomy pouch
13: stop portion
14: flange
15: gas releasing portion
16: outlet
20: feces treatment agent for colostomy 101: stoma portion
103: right hand
102: left hand

The invention claimed is:

1. A feces treatment agent for colostomy comprising an agent A contained in a water-soluble base material, wherein the agent A includes:
   (1) carboxymethyl cellulose as a granular water-soluble lubricant in an amount of 3.0 to 10.0 mass %,
   (2) polyacrylic acid or a salt thereof as a granular water-absorbing gelling agent in an amount of 15.0 to 25.0 mass %,
   (3) sodium bicarbonate in an amount of 50.0 to 70.0 mass %, and
   (4) zinc oxide in an amount of 10.0 to 20.0 mass %, and
   wherein an average particle diameter of the granular water-absorbing gelling agent is 20 to 40 μm.

2. The feces treatment agent for colostomy according to claim 1, further comprising (5) a component including at least one selected from the group consisting of lignin, slaked lime and limestone.

3. The feces treatment agent for colostomy according to claim 2,
   wherein the component (5) is slaked lime or limestone.

4. The feces treatment agent for colostomy according to claim 1,
   wherein the granular water-soluble lubricant has gelation ability, and
   an onset of gelation of the granular water-absorbing gelling agent is earlier than an onset of gelation of the granular water-soluble lubricant.

5. The feces treatment agent for colostomy according to claim 1, wherein the granular water-absorbing gelling agent starts gelling within a minute.

6. The feces treatment agent for colostomy according to claim 1, wherein the feces treatment agent for colostomy does not comprise water.

7. The feces treatment agent for colostomy according to claim 1, wherein the granular water-soluble lubricant is included in an amount of 5.0 to 10.0 mass % in the agent A.

8. The feces treatment agent for colostomy according to claim 1, wherein the sodium bicarbonate is included in an amount of 56.5 to 70.0 mass % in the agent A.

9. A kit of a feces treatment agent for colostomy, comprising:
   the feces treatment agent for colostomy according to claim 1; and
   a container to contain water.

10. A method for treating feces in a colostomy pouch by separately adding the feces treatment agent for colostomy according to claim 1 and water to the colostomy pouch.

11. The feces treatment agent for colostomy according to claim 1, wherein the water-soluble base material contributes to gelation by contact with water.

12. The feces treatment agent for colostomy according to claim 1,
   wherein the water-soluble base material is in a form of a pouch, and the pouch is sealed.

13. The feces treatment agent for colostomy according to claim 1, wherein the average particle diameter of the granular water-absorbing gelling agent is 26 to 35 μm.

14. The feces treatment agent for colostomy according to claim 1, wherein the amount of the carboxymethyl cellulose is in a range of 5.0 to 10.0 mass %, and
   the amount of sodium bicarbonate is in a range of 56.5 to 70.0 mass %.

\* \* \* \* \*